United States Patent [19]

Willms et al.

[11] Patent Number: 5,073,185

[45] Date of Patent: Dec. 17, 1991

[54] HETEROCYCLICALLY SUBSTITUTED N-SULTAMSULFONAMIDES

[75] Inventors: Lothar Willms, Hillscheid; Klaus Bauer, Hanau; Hermann Bieringer, Eppstein/Taunus; Helmut Bürstell, Frankfurt am Main, all of Fed. Rep. of Germany

[73] Assignee: Hoechst Aktiengesellschaft, Frankfurt am Main, Fed. Rep. of Germany

[21] Appl. No.: 493,946

[22] Filed: Mar. 15, 1990

Related U.S. Application Data

[62] Division of Ser. No. 263,817, Oct. 28, 1988, Pat. No. 4,925,480.

[30] Foreign Application Priority Data

Oct. 31, 1987 [DE] Fed. Rep. of Germany ....... 3736959

[51] Int. Cl.$^5$ .................... A01N 43/66; C07D 417/12
[52] U.S. Cl. ...................... 71/091; 544/198; 544/212; 544/207; 544/209; 544/3; 540/467; 540/544
[58] Field of Search ................ 71/91; 544/198, 212, 544/207, 209, 3; 540/467, 544

[56] References Cited

U.S. PATENT DOCUMENTS 4,534,790 8/1985 Wolf ........................................ 71/93
4,718,937 1/1988 Willms et al. ........................ 71/93

FOREIGN PATENT DOCUMENTS 0107979 5/1984 European Pat. Off. .
0131258 6/1984 European Pat. Off. .
0202762 11/1986 European Pat. Off. .

OTHER PUBLICATIONS

Makino et al., Chemical Abstracts vol. 112, entry 216980y (1990).

*Primary Examiner*—John M. Ford

[57] ABSTRACT

Compounds of the formula I or their salts

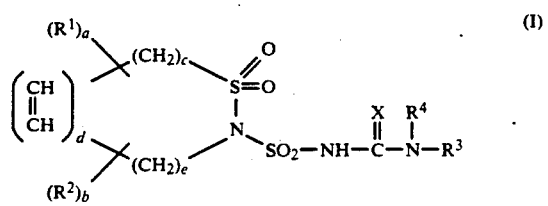

wherein
$R^1$ and $R^2$ denote H, halogen, alkyl, alkenyl, alkynyl or alkoxy, which can be substituted, or denote —(CH$_2$)$_n$—COOR$^{11}$;
$R^3$ denotes H, alkyl, alkenyl or alkynyl;
$R^4$ denotes a heterocyclic radical of the formulae

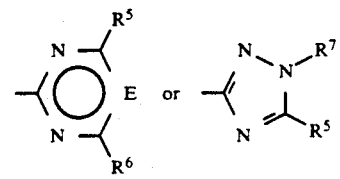

where E is CH or N; X is O or S and a, b, c, d, e in each case denote 0, 1 or 2, with the proviso that c+d+e≧2, possess excellent herbicidal and plant growth-regulating properties.

11 Claims, No Drawings

HETEROCYCLICALLY SUBSTITUTED N-SULTAMSULFONAMIDES

This application is a division of application Ser. No. 07/263,817, filed Oct. 28, 1988, now U.S. Pat. No. 4,925,480.

DESCRIPTION

It is known that heterocyclically substituted sulfonylureas show herbicidal and plant growth-regulating properties (for example EP-A-131,258).

However, they show disadvantages upon use, such as, for example, high persistence or insufficient selectivity.

It has now been found that heterocyclically substituted N-sultamsulfonamides are particularly suitable as herbicides and plant growth regulators.

The present invention thus relates to compounds of the formula (I) or their salts

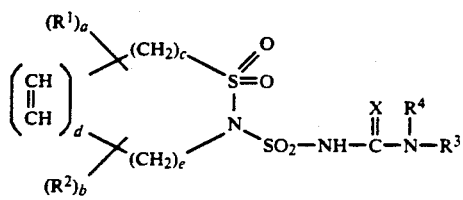

in which $R^1$ and $R^2$ independently of one another denote hydrogen, halogen, $(C_1-C_8)$-alkyl, $(C_2-C_8)$-alkenyl, $(C_2-C_8)$-alkynyl or $(C_1-C_8)$-alkoxy, it being possible for these radicals to be optionally substituted once or more than once by halogen or to be substituted once or twice by $(C_1-C_4)$-alkoxy or $(C_1-C_4)$-alkylthio; or denotes $-(CH_2)_n-COOR^{11}$, where n denotes a number between 0 and 2, $R^3$ denotes hydrogen; $(C_1-C_8)$-alkyl; $(C_2-C_8)$-alkenyl or $(C_2-C_8)$-alkynyl, $R^4$ denotes a heterocyclic radical of the formulae

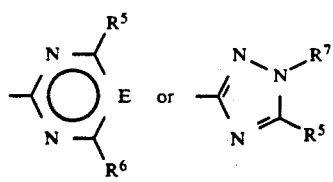

where E is CH or N, $R^5$ and $R^6$ independently of one another denote hydrogen; halogen; $(C_1-C_4)$-alkyl or $(C_1-C_4)$-alkoxy, both of which can optionally be halogenated once or more than once; di-$[(C_1-C_4)$-alkoxy$]$-$(C_1-C_2)$-alkyl; $(C_3-C_6)$-cycloalkyl, $-OCHR^8COOR^9$; $-NR^9R^{10}$ or $(C_1-C_4)$-alkylthio, $R^7$ denotes $(C_1-C_4)$-alkyl, $R^8$ denotes hydrogen or $(C_1-C_4)$-alkyl and $R^9$ and $R^{10}$ independently of one another denote hydrogen; $(C_1-C_4)$-alkyl; $(C_2-C_4)$-alkenyl or $(C_2-C_4)$-alkynyl $R^{11}$ denotes hydrogen, $(C_1-C_8)$-alkyl, $(C_2-C_4)$-alkenyl or $(C_2-C_4)$-alkynyl, each of which can optionally be substituted once or more than once by halogen or $(C_1-C_4)$-alkoxy radicals, X denotes oxygen or sulfur and a, b, c, d and e independently of one another denote the number 0, 1 or 2, with the proviso that the total of c+d+e is larger than, or equal, 2.

The compounds of the formula I can form salts in which the hydrogen of the $-SO_2-NH-$ group is replaced by a cation suitable for agriculture. In general, these salts are metal salts, in particular alkali metal salts, alkaline earth metal salts, or optionally alkylated ammonium salts or organic amine salts. They are preferably prepared in inert solvents, such as, for example, water, methanol or acetone, at temperatures of from 0° to 100° C. Suitable bases for the preparation of the salts according to the invention are, for example, alkali metal carbonates, such as potassium carbonates, alkali metal hydroxides and alkaline earth metal hydroxides, ammonia or ethanolamine.

Preferred compounds of the formula I are those in which $R^1$ and $R^2$ independently of one another denote hydrogen, $(C_1-C_4)$-alkyl which is substituted as described above, or halogen; a, b, c, d and e independently of one another denote the numbers 0, 1 or 2, but, with the proviso that $c+d+e \geq 2$ and $\geq 4$, $R^3$ denotes hydrogen, $(C_1-C_4)$-alkyl or allyl; $R^4$ denotes a radical of the formula

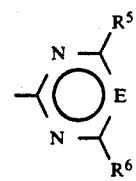

and $R^5$ and $R^6$ independently of one another denote halogen, $(C_1-C_4)$-alkyl or $(C_1-C_4)$-alkoxy, both of which can be substituted by halogen, and X stands for oxygen.

Halogen preferably denotes fluorine, chlorine or bromine. Halogenated alkyl or halogenated alkoxy are taken to mean, in particular, the radicals $CF_3$, $CH_2-CH_2Cl$, $CH_2CH_2Br$, $OCF_2H$ and $OCH_2CF_3$. Halogenated alkenyl or halogenated alkynyl denotes, in particular, $CH_2CH=CHCl$, $CH_2CCl=CCl_2$ and $CH_2-C\equiv CCH_2-Cl$. $(C_3-C_6)$Cycloalkyl denotes, in particular, cyclopropyl. Particularly preferred compounds of the formula (I) are those in which $R^1$ and/or $R^2$ denote(s) hydrogen and $(C_1-C_4)$-alkyl which is substituted as described above, $R^3$ denotes hydrogen, a+b is 0, 1 or 2, d is 0, c+e is 3 or 4, in particular 4, $R^4$ denotes a radical of the formula

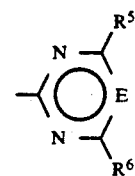

and $R^5$ and $R^6$ independently of one another denote chlorine, bromine, $(C_1-C_4)$-alkyl, $(C_1-C_4)$-alkoxy, $OCF_2H$, $OCH_2CF_3$ or $CF_3$, and their salts.

The present invention further relates to a process for the preparation of compounds of the general formula (I), which comprises (a) reacting a compound of the formula (II)

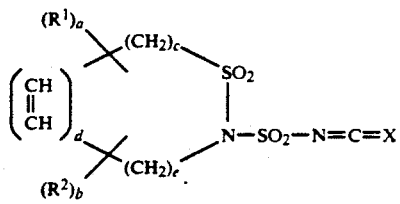

with a compound of the formula (III)

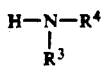

(b) when X is oxygen, reacting a compound of the formula (IV)

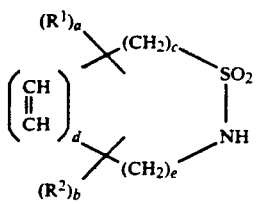

with a chlorosulfonylurea of the formula (V)

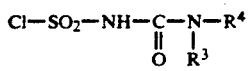

and, if appropriate, converting the resulting compound into a salt thereof.

The compounds of the formulae (II) and (III) are preferably reacted in inert aprotic solvents, such as, for example, acetonitrile, dichloromethane, toluene, tetrahydrofuran or dioxane, at temperatures between 0° C. and the boiling temperature of the solvent.

The N-sultamsulfonyl isocyanates of the formula II are novel and can be prepared by reacting the sultams of the formula II with chlorosulfonyl isocyanate. Thus, the compounds of the formula II and the process for their preparation also constitute a part of the present invention. This process is preferably carried out in inert organic solvents, such as, for example, toluene, xylene or chlorobenzene, following the known reaction of open-chain secondary sulfonamides with chlorosulfonyl isocyanate (German Offenlegungsschrift 2,257,240).

The reaction of the compounds (IV) with the chlorosulfonylureas (V) is preferably carried out in inert solvents, such as, for example, dichloromethane, acetonitrile, tetrahydrofuran, dioxane or dimethoxyethane, at temperatures of from −70° C. to 150° C., if appropriate in the presence of a base as the HCl-binding agent. Bases which can be employed include alkali metal carbonates, alkali metal bicarbonates, alkaline earth metal carbonates or alkaline earth metal bicarbonates, such as, for example, $K_2CO_3$, $NaHCO_3$ and $Na_2CO_3$, or tertiary amines, such as, e.g. pyridine or triethylamine.

The sultams (V) are known from the literature or can be prepared by processes known from the literature (cf., for example, Liebigs Ann. 646 (1961), pp. 32–45; Liebigs Ann. 651 (1962), pp. 17–29; C.A. 89 (1978), 179478 Z; Bull. Chem. Soc. Jap. 44 (1971), 771–777, Tetr. Lett. (1972), p. 213; Chem. Ber. 93 (1960), p. 784). The chlorosulfonylureas (V) are accessible from the amines of the formula (III) and chlorosulfonyl isocyanate (EP-A 141,199).

The starting substances of the formula (III) are known or can be prepared by processes known in principle, for example by cyclizing the corresponding guanidine derivatives with appropriately substituted 1,3-diketones, compare for e ample "The Chemistry of Heterocyclic Compounds", Volume XVI (1962) and Supplement I (1970), or by derivatizing cyanuric chloride, cf., for example, "The Chemistry of Heterocyclic Compounds", L. Rapaport: "s-Triazines and Derivatives" (1959).

The compounds of the formula I according to the invention show an excellent herbicidal activity against a broad range of economically important monocotyledon and dicotyledon weeds. The active substances also have a good action against perennial weeds which produce shoots from rhizomes, root stocks or other perennial organs and which cannot be easily controlled. In this context, it does not matter if the substances are applied before sowing, or using the pre-emergence or post-emergence method. Some representatives of the monocotyledon and dicotyledon weed flora which can be controlled by the compounds according to the invention may be mentioned individually as examples, but this naming is not to be taken to mean a restriction to certain species.

The monocotyledon weed species which are well controlled include, for example, Avena, Lolium, Alopecurus, Phalaris, Echinochloa, Digitaria, Setaria etc. and Cyperus species from the annual group, and the perennial species include Agropyron, Cynodon, Imperata and Sorghum etc., and also perennial Cyperus species.

Of the dicotyledon weed species, the range of action covers species such as, for example, Galium, Viola, Veronica, Lamium, Stellaria, Amaranthus, Sinapis, Ipomoea, Matricaria, Abutilon, Sida etc. from the annual plants, and Convolvulus, Cirsium, Rumex, Artemisia etc. from the perennials.

The weeds occurring under the specific culture conditions in rice, such as, for example, Sagittaria, Alisma, Eleocharis, Scirpus, Cyperus etc., are also very well controlled by the active substances according to the invention.

If the compounds according to the invention are applied to the soil surface before germination, either emergence of the weed seedlings is prevented completely, or the weeds grow until they have reached the cotyledon stage but growth then ceases and, after a period of three to four weeks, the plants eventually die completely. When the active substances are applied using the post-emergence method to the green parts of the plants, growth also stops dramatically very soon after treatment, and the weeds remain in the growth stage at the time of application, or, after a certain period of time, die more or less rapidly so that competition from the weeds, which is detrimental for the crop plants, can thus be prevented at a very early stage and in a sustained manner by using the new compounds according to the invention.

Even though the compounds according to the invention have an excellent herbicidal activity against monocotyledon and dicotyledon weeds, crop plants of economically important crops such as, for example, wheat, barley, rye, rice, maize, sugar beet, cotton and soya beans, are damaged to a negligible extent only, or not at all. Thus, the present compounds are very suitable for selectively controlling undesired plant growth in agricultural crops.

In addition, the compounds according to the invention have growth-regulating properties in crop plants. They engage in the plant metabolism in a regulating manner and can thus be employed for facilitating harvesting, such as, for example, by initiating desiccation, abscission and stunted growth. Furthermore, they are also suitable for generally regulating and inhibiting undesired vegetative growth without simultaneously destroying the plants.

Inhibition of vegetative growth plays an important role in many monocotyledon and dicotyledon crops because lodging can hereby be reduced, or prevented completely.

The agents according to the invention can be employed in the conventional preparations as wettable powders, emulsifiable concentrates, sprayable solutions, dusting agents, seed dressing agents, dispersions, granules or microgranules.

Wettable powders are preparations which are uniformly dispersible in water and which, besides the active substance, also contain wetting agents, for example, polyoxyethylated alkylphenols, polyoxyethylated fatty alcohols, alkylsulfonates or alkylphenylsulfonates, and dispersing agents, for example sodium ligninsulfonate, sodium 2,2'-dinaphthylmethane-6,6'-disulfonate, sodium dibutylnaphthalenesulfonate and also sodium oleoylmethyltaurate, in addition, if appropriate, to a diluent or inert substance. They are prepared in a customary manner, for example by grinding and mixing of the components.

Emulsifiable concentrates can be prepared for example by dissolving the active substance in an inert organic solvent, for example butanol, cyclohexanone, dimethylformamide, xylene and also higher-boiling aromatics or hydrocarbons, with the addition of one or more emulsifiers. In the case of liquid active substances, all or some of the solvent can also be omitted. Emulsifiers which can be used are, for example: calcium salts of alkylarylsulfonic acids, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, fatty alcohol/propylene oxide/ethylene oxide condensation products, alkyl polyglycol ethers, sorbitan fatty acid esters, polyoxyethylene sorbitan fatty acid esters or polyoxyethylene sorbitol esters.

Dusting agents can be obtained by grinding the active substance with finely divided solid substances, for example talc or natural clays, such as kaolin, bentonite, pyrophillite or diatomaceous earth.

Granules can be produced either by spraying the active substance onto adsorptive, granulated inert material or by applying active substance concentrates onto the surface of excipients such as sand, kaolinites or granulated inert material, by means of binders, for example polyvinyl alcohol, sodium polyacrylate or alternatively mineral oils. Suitable active substances can also be granulated in the manner which is conventional for the preparation of fertilizer granules, if desired mixed with fertilizers.

The active substance concentration in wettable powders is, for example, about 10 to 90% by weight, the remainder to 100% by weight comprising conventional formulation components. In the case of emulsifiable concentrates, the active substance concentration can be about 5 to 80% by weight. Dust-form formulations usually contain 5 to 20% by weight of active substance, and sprayable solutions about 2 to 20% by weight. In the case of granules, the active substance content depends partly on whether the active compound is liquid or solid and on which granulation auxiliaries, fillers etc. are used.

In addition, the active substance formulations mentioned contain, if appropriate, the adhesives, wetting agents, dispersing agents, emulsifiers, penetrants, solvents, fillers or excipients which are conventional in each case.

For use, the concentrates, present in commercially available form, are diluted, if appropriate, in a conventional manner, for example using water in the case of wettable powders, emulsifiable concentrates, dispersions and, in some cases also for microgranules. Dust-form and granulated preparations and also sprayable solutions are usually not further diluted with other inert substances before use.

The application rate required varies with the external conditions, such as temperature and humidity, amongst others. It can vary within wide limits, for example from 0.005 to 10.0 kg/ha or more of active substances; preferably, however, it is from 0.01 to 5 kg/ha.

If appropriate, mixtures or mixed formulations with other active substances, such as, for example, insecticides, acaricides, herbicides, fertilizers, growth regulators or fungicides are also possible.

The following examples illustrate the invention in greater detail.

Formulation Examples

A. A dusting agent is obtained by mixing 10 parts by weight of active substance and 90 parts by weight of talc or inert substance, and comminuting the mixture in a hammer mill.

B. A wettable powder which is readily dispersible in water is obtained by mixing 25 parts by weight of active substance, 64 parts by weight of kaolin-containing quartz as inert substance, 10 parts by weight of potassium ligninsulfonate and 1 part by weight of sodium oleoylmethyltaurate as wetting and dispersing agent, and grinding the mixture in a pin disk mill.

C. A dispersion concentrate which is readily dispersible in water is obtained by mixing 20 parts by weight of active substance with 6 parts by weight of alkylphenol polyglycol ether (Triton X 207), 3 parts by weight of isotridecanol polyglycol ether (8 EO) and 71 parts by weight of paraffinic mineral oil (boiling range, for example, about 255° to above 377° C.), and grinding the mixture in a ball mill to a fineness of below 5 microns.

D. An emulsifiable concentrate is obtained from 15 parts by weight of active substance, 75 parts by weight of cyclohexanone as solvent and 10 parts by weight of oxyethylated nonylphenol (10 EO) as emulsifier.

CHEMICAL EXAMPLES

Example 1

N-(1,4-Butanesultam)-sulfonyl isocyanate

A solution of 7.78 g (0.055 mol) of chlorosulfonyl isocyanate in 20 ml of absolute chlorobenzene is added dropwise at 0° C. to a suspension of 6.78 g (0.05 mol) of 1,4-butanesultam—prepared in accordance with Liebigs Ann. 651 (1962), p. 26 —in 80 ml of absolute chlorobenzene. When the dropwise addition is complete, the temperature is slowly increased to 125°-130° C., and the mixture is heated for about 6 h at 130° C. The mixture is cooled and the solvent is removed on a rotary evaporator. The oil remaining (12.0 g≙100% of theory) is employed without purification.

Example 2
1-[N-(1,4-Butanesultam)sulfonyl]-3-(4,6-dimethyl-pyrimidin-2-yl)-urea A solution of 6.24 g (0.026 mol) of N-(1,4-butanesultam)sulfonyl isocyanate in 20 ml of dichloromethane is added dropwise at 0° C. to 3.08 g (0.025 mol) of 2-amino-4,6-dimethylpyrimidine in 80 ml of absolute dichloroomethane. The mixture is allowed to warm to room temperature, and stirring is continued for 18 hours. The reaction solution is washed with 0.5N hydrochloric acid and water and dried over sodium sulfate, and the solvent is then removed on a rotary evaporator. The oil remaining is crystallized from dichloromethane/n-heptane. 8.36 g (92% of theory) of 1-[N-(1,4-butanesultam)-sulfonyl]-3-(4,6-dimethyl-pyrimidin-2-yl)-urea of m.p. 145°-147° C. are obtained.

Example 3
1-[N-(1,3-Propanesultam)-sulfonyl]-3-(4,6-dimethyl-pyrimidin-2-yl)-urea 2.2 ml (0.025 mol) of chlorosulfonyl isocyanate are initially introduced into 100 ml of absolute acetonitrile at 40° C., and 3.88 g (0.025 mol) of 2-amino-4,6-dimethoxypyrimidine is added under nitrogen. This suspension is stirred at 0° C. for about 1 h and cooled to −40° C., and 3.07 g (0.025 mol) of 1,3-propanesultam, dissolved in 20 ml of absolute CH$_3$CN, are added. The mixture is allowed to warm to room temperature in the course of 4 h, and stirring is continued for 18 h at room temperature. The residue is filtered off with suction and suspended in 50 ml of absolute acetonitrile at 0° C., and 3.5 ml (0.025 mol) of triethylamine are added. The mixture is stirred for 2 h at room temperature, and the residue is filtered off with suction, washed with water and dried in vacuo. 9.21 g (96.6% of theory) of 1-[N-(1,3-propanesultam)-sulfonyl]-3-(4,6-dimethoxy-pyrimidin-2-yl)-urea of m.p. 166°-170° C. are obtained.

TABLE 1

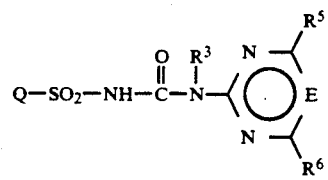

| Example | Q | R$^3$ | R$^5$ | R$^6$ | E | m.p. |
|---|---|---|---|---|---|---|
| 4 | ⌈ SO$_2$ <br> ⌊ N— | H | CH$_3$ | CH$_3$ | CH | |
| 5 | ⌈ SO$_2$ <br> ⌊ N— | H | OCH$_3$ | CH$_3$ | CH | |
| 6 | ⌈ SO$_2$ <br> ⌊ N— | H | OCH$_3$ | OCH$_3$ | CH | 40-44 |
| 7 | ⌈ SO$_2$ <br> ⌊ N— | H | OCH$_3$ | Cl | CH | |
| 8 | ⌈ SO$_2$ <br> ⌊ N— | H | OC$_2$H$_5$ | OCH$_3$ | CH | |
| 9 | ⌈ SO$_2$ <br> ⌊ N— | H | OCHF$_2$ | OCH$_3$ | CH | |
| 10 | ⌈ SO$_2$ <br> ⌊ N— | H | OCHF$_2$ | OCHF$_2$ | CH | |
| 11 | ⌈ SO$_2$ <br> ⌊ N— | H | OCH$_2$CF$_3$ | OCH$_3$ | CH | |
| 12 | ⌈ SO$_2$ <br> ⌊ N— | H | CH$_3$ | Cl | CH | |
| 13 | ⌈ SO$_2$ <br> ⌊ N— | H | CH$_3$ | CH$_3$ | N | |

TABLE 1-continued $$Q-SO_2-NH-\underset{\underset{O}{\|}}{C}-\underset{\underset{R^3}{|}}{N}-\text{[ring with N, N, E, } R^5, R^6\text{]}$$

| Example | Q | $R^3$ | $R^5$ | $R^6$ | E | m.p. |
|---|---|---|---|---|---|---|
| 14 | [SO₂–N– ring] | H | OCH₃ | CH₃ | N | |
| 15 | [SO₂–N– ring] | H | OCH₃ | OCH₃ | N | |
| 16 | CH₃–[SO₂–N– ring] | H | CH₃ | CH₃ | CH | |
| 17 | CH₃–[SO₂–N– ring] | H | OCH₃ | CH₃ | CH | |
| 18 | CH₃–[SO₂–N– ring] | H | OCH₃ | OCH₃ | CH | 68–71 |
| 19 | CH₃–[SO₂–N– ring] | CH₃ | OCH₃ | OCH₃ | CH | |
| 20 | CH₃–[SO₂–N– ring] | H | OCH₃ | Cl | CH | |
| 21 | CH₃–[SO₂–N– ring] | H | OCH₃ | NHCH₃ | CH | |
| 22 | CH₃–[SO₂–N– ring] | H | OCH₃ | Br | CH | |
| 23 | CH₃–[SO₂–N– ring] | H | OCH₃ | SCH₃ | CH | |
| 24 | CH₃–[SO₂–N– ring] | H | OCHF₂ | OCH₃ | CH | |
| 25 | CH₃–[SO₂–N– ring] | H | OCH₃ | CH₃ | N | |
| 26 | CH₃–[SO₂–N– ring] | H | OC₂H₅ | NHCH₃ | N | |
| 27 | CH₃–[SO₂–N– ring] | H | OCH₃ | N(CH₃)₂ | N | |
| 28 | CH₃,CH₃–[SO₂–N– ring] | H | CH₃ | CH₃ | CH | |
| 29 | CH₃,CH₃–[SO₂–N– ring] | H | OCH₃ | CH₃ | CH | |

TABLE 1-continued

Q—SO₂—NH—C(=O)—N(R³)—[ring with R⁵, R⁶, E, N, N]

| Example | Q | R³ | R⁵ | R⁶ | E | m.p. |
|---------|---|----|----|----|----|------|
| 30 | (CH₃)₂C(SO₂)(N—) | H | OCH₃ | OCH₃ | CH | 131–133 |
| 31 | (CH₃)₂C(SO₂)(N—) | CH₃ | OCH₃ | CH₃ | CH | |
| 32 | (CH₃)₂C(SO₂)(N—) | H | OCH₃ | Cl | CH | |
| 33 | (CH₃)₂C(SO₂)(N—) | H | OCHF₂ | OCHF₂ | CH | |
| 34 | (CH₃)₂C(SO₂)(N—) | H | SCH₃ | CH₃ | CH | |
| 35 | (CH₃)₂C(SO₂)(N—) | H | CH(OCH₃)₂ | OCH₃ | CH | |
| 36 | (CH₃)₂C(SO₂)(N—) | H | OCH₃ | CH₃ | N | |
| 37 | (CH₃)₂C(SO₂)(N—) | H | OCH₃ | OCH₃ | N | |
| 38 | (CH₃)₂C(SO₂)(N—) | H | NH₂ | OCH₃ | N | |
| 39 | (CH₃)₂C(SO₂)(N—) | CH₃ | OCH₃ | CH₃ | N | |
| 40 | C₂H₅CH(SO₂)(N—) | H | OCH₃ | OCH₃ | CH | |
| 41 | C₂H₅CH(SO₂)(N—) | H | OCH₃ | CH₃ | CH | |

TABLE 1-continued $$Q-SO_2-NH-\overset{O}{\underset{}{C}}-\underset{}{\overset{R^3}{N}}-\underset{R^6}{\overset{R^5}{\underset{N}{\bigcirc}}}E$$

| Example | Q | $R^3$ | $R^5$ | $R^6$ | E | m.p. |
|---|---|---|---|---|---|---|
| 42 | $C_2H_5$–CH–N– with $SO_2$ | H | $CH_3$ | $CH_3$ | CH | |
| 43 | $C_2H_5$–CH–N– with $SO_2$ | H | $OCH_3$ | $CH_3$ | N | |
| 44 | $(CH_3)_2CH$–CH–N– with $SO_2$ | H | $OCH_3$ | $OCH_3$ | CH | |
| 45 | $(CH_3)_2CH$–CH–N– with $SO_2$ | H | $OCH_3$ | Cl | CH | |
| 46 | $(CH_3)_2CH$–CH–N– with $SO_2$ | H | $OCH_3$ | $CH_3$ | CH | |
| 47 | $CH_3O$–CH–N– with $SO_2$ | H | $OCH_3$ | $OCH_3$ | CH | |
| 48 | $CH_3O$–CH–N– with $SO_2$ | H | $CH_3$ | $CH_3$ | CH | |
| 49 | $CH_3O$–CH–N– with $SO_2$ | H | $OCH_3$ | Cl | CH | |
| 50 | $CH_3OCH_2$–CH–N– with $SO_2$ | H | $OCH_3$ | $OCH_3$ | CH | |
| 51 | $CH_3OCH_2$–CH–N– with $SO_2$ | H | $OCH_3$ | $CH_3$ | N | |
| 52 | $CH_3OOC$–CH–N– with $SO_2$ | H | $OCH_3$ | $OCH_3$ | CH | 110–111 |
| 53 | $CH_3OOC$–CH–N– with $SO_2$ | H | $OCH_3$ | $OCH_3$ | CH | |
| 54 | $CH_3OOC$–CH–N– with $SO_2$ | H | $OCH_3$ | Cl | CH | |

TABLE 1-continued

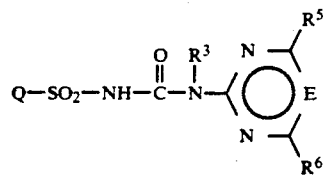

| Example | Q | $R^3$ | $R^5$ | $R^6$ | E | m.p. |
|---|---|---|---|---|---|---|
| 55 | CH₃OOC–[SO₂/N–] | H | OC₂H₅ | Cl | CH | |
| 56 | CH₃–[SO₂/N–], CH₃OOC | H | OCH₃ | OCH₃ | CH | |
| 57 | CH₃–[SO₂/N–], CH₃OOC | H | OCH₃ | CH₃ | N | |
| 58 | C₂H₅OOC–[SO₂/N–] | H | OCH₃ | OCH₃ | CH | |
| 59 | C₂H₅OOC–[SO₂/N–] | H | CH₃ | CH₃ | CH | |
| 60 | C₂H₅OOC–[SO₂/N–] | H | OCH₃ | OCH₃ | N | |
| 61 | CH₃OOCCH₂–[SO₂/N–] | H | OCH₃ | OCH₃ | CH | |
| 62 | CH₃OOCCH₂–[SO₂/N–] | H | OCH₃ | ClCH₂ | N | |
| 63 | C₂H₅OOCCH₂–[SO₂/N–] | H | OCH₃ | OCH₃ | CH | |
| 64 | CH₃–[SO₂/N–] | H | OCH₃ | OCH₃ | CH | |
| 65 | CH₃–[SO₂/N–] | H | OCH₃ | CH₃ | CH | |
| 66 | CH₃–[SO₂/N–] | H | CH₃ | CH₃ | CH | |
| 67 | CH₃–[SO₂/N–] | CH₃ | OCH₃ | CH₃ | N | |

TABLE 1-continued $$Q-SO_2-NH-\overset{O}{\underset{}{C}}-\underset{}{\overset{R^3}{N}}-\text{[ring with } N, N, E, R^5, R^6\text{]}$$

| Example | Q | $R^3$ | $R^5$ | $R^6$ | E | m.p. |
|---|---|---|---|---|---|---|
| 68 | CH$_3$—SO$_2$—N— | C$_2$H$_5$ | OCH$_3$ | OCH$_3$ | N | |
| 69 | CH$_3$—SO$_2$—N— | H | OCH$_3$ | CH$_3$ | N | |
| 70 | CH$_3$—SO$_2$—N— | H | OC$_2$H$_5$ | NHCH$_3$ | N | |
| 71 | CH$_3$—SO$_2$—N— | H | OCH$_3$ | NHCH$_3$ | CH | |
| 72 | CH$_3$—SO$_2$—N— | H | Cl | SCH$_3$ | CH | |
| 73 | CH$_3$—SO$_2$—N— | H | Cl | OCH$_3$ | CH | |
| 74 | CH$_3$—SO$_2$—N— | H | OCHF$_2$ | OCHF$_2$ | CH | |
| 75 | CH$_3$—SO$_2$—N— | H | cyclopropyl | OCH$_3$ | N | |
| 76 | (CH$_3$)$_2$—SO$_2$—N— | H | OCH$_3$ | OCH$_3$ | CH | |
| 77 | (CH$_3$)$_2$—SO$_2$—N— | H | OCH$_3$ | OCH$_3$ | CH | |
| 78 | (CH$_3$)$_2$—SO$_2$—N— | H | OCH$_3$ | Cl | CH | |
| 79 | (CH$_3$)$_2$—SO$_2$—N— | H | OCH$_3$ | CH$_3$ | N | |
| 80 | C$_2$H$_5$—SO$_2$—N— | H | OCH$_3$ | OCH$_3$ | CH | |
| 81 | C$_2$H$_5$—SO$_2$—N— | H | OCH$_3$ | Cl | CH | |
| 82 | C$_2$H$_5$—SO$_2$—N— | H | OCHCF$_2$ | OCH$_3$ | CH | |
| 83 | C$_2$H$_5$—SO$_2$—N— | H | CH$_3$ | CH$_3$ | CH | |

TABLE 1-continued $$Q-SO_2-NH-\underset{\underset{O}{\|}}{C}-\underset{R^3}{N}-\underset{\underset{R^6}{N}}{\overset{R^5}{\underset{\|}{N}}}E$$

| Example | Q | $R^3$ | $R^5$ | $R^6$ | E | m.p. |
|---|---|---|---|---|---|---|
| 84 | $(C_2H_5)_2N-SO_2-$ | H | $OCH_3$ | $OCH_3$ | CH | |
| 85 | $(C_2H_5)_2N-SO_2-$ | H | $OCH_3$ | Cl | CH | |
| 86 | $(CH_3)_2CH-SO_2-N-$ | H | $OCH_3$ | $OCH_3$ | CH | |
| 87 | $(CH_3)_2CH-SO_2-N-$ | H | $OCH_3$ | $CH_3$ | N | |
| 88 | $ClCH_2-SO_2-N-$ | H | $OCH_3$ | $OCH_3$ | CH | |
| 89 | $ClCH_2-SO_2-N-$ | H | $OCH_3$ | $CH_3$ | CH | |
| 90 | $ClCH_2-SO_2-N-$ | H | $OCH_3$ | $CH_3$ | N | |
| 91 | $CCl_3-SO_2-N-$ | H | $OCH_3$ | $OCH_3$ | CH | |
| 92 | $CCl_3-SO_2-N-$ | H | $OCH_3$ | Cl | CH | |
| 93 | $CF_3-SO_2-N-$ | H | $OCH_3$ | $OCH_3$ | CH | |
| 94 | $CF_3-SO_2-N-$ | H | $CH_3$ | $CH_3$ | CH | |
| 95 | $CF_3-SO_2-N-$ | H | $OCH_3$ | $CH_3$ | N | |
| 96 | $CCl_3-SO_2-N-$ | H | $OCH_3$ | $OCH_3$ | CH | |
| 97 | $CCl_3-SO_2-N-$ | H | $CH_3$ | $CH_3$ | CH | |
| 98 | $CF_3-SO_2-N-$ | H | $OCH_3$ | $OCH_3$ | CH | |
| 99 | $CF_3-SO_2-N-$ | H | $OCH_3$ | $CH_3$ | CH | |

TABLE 1-continued $$Q-SO_2-NH-\overset{O}{\underset{\parallel}{C}}-\underset{R^3}{N}-\underset{\underset{R^6}{\diagup}}{\overset{\overset{R^5}{\diagdown}}{\diagdown}}\!\!\!\!\!\!\!\underset{N}{\overset{N}{\diagup}}\!\!\!E$$

| Example | Q | $R^3$ | $R^5$ | $R^6$ | E | m.p. |
|---|---|---|---|---|---|---|
| 100 |  | H | $OCH_3$ | $CH_3$ | CH | |
| 101 |  | H | $CH_3$ | $CH_3$ | CH | 161–163 |
| 102 |  | H | $OCH_3$ | Cl | CH | 148–149 |
| 103 |  | H | $CH_3$ | Cl | CH | |
| 104 |  | H | $OCHF_2$ | Cl | CH | |
| 105 |  | H | $OCHF_2$ | $OCH_3$ | CH | |
| 106 |  | H | $OCHF_2$ | $OCHF_2$ | CH | |
| 107 |  | H | $OC_2H_5$ | Cl | CH | |
| 108 |  | H | $OC_2H_5$ | $CH_3$ | CH | |
| 109 |  | H | $OC_2H_5$ | $OCH_3$ | CH | |
| 110 |  | H | $OCH_3$ | $SCH_3$ | CH | |
| 111 |  | H | $OCH_3$ |  | CH | |

TABLE 1-continued
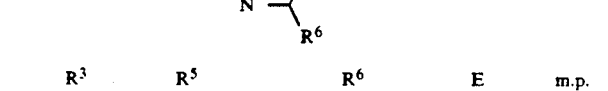
| Example | Q | R³ | R⁵ | R⁶ | E | m.p. |
|---|---|---|---|---|---|---|
| 112 |  | H | OCH₃ | NHCH₃ | CH | |
| 113 |  | H | OCH₃ | H(CH₃)₂ | CH | |
| 114 |  | H | OCH₃ | NH₂ | CH | |
| 115 |  | CH₃ | OCH₃ | OCH₃ | CH | |
| 116 |  | CH₃ | OCH₃ | CH₃ | CH | |
| 117 |  | CH₂<br>CH=CH₂ | OCH₃ | OCH₃ | CH | |
| 118 |  | OCH₃ | OCH₃ | OCH₃ | CH | |
| 119 |  | H | OCH₃ | OCH₃ | N | |
| 120 |  | H | OCH₃ | CH₃ | N | |
| 121 |  | H | CH₃ | CH₃ | N | |
| 122 |  | H | OCH₃ | NHCH₃ | N | |
| 123 |  | H | OCH₃ | N(CH₃)₂ | N | |

TABLE 1-continued
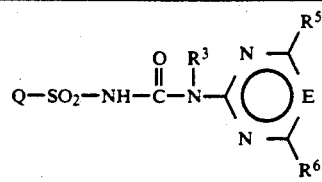
| Example | Q | $R^3$ | $R^5$ | $R^6$ | E | m.p. |
|---|---|---|---|---|---|---|
| 124 | ⌇SO₂N— | H | OC$_2$H$_5$ | NHCH$_3$ | N | |
| 125 | ⌇SO₂N— | H | OCH$_3$ | OCH$_2$CF$_3$ | N | |
| 126 | ⌇SO₂N— | H | OCH$_3$ | OCHF$_2$ | N | |
| 127 | ⌇SO₂N— | H | OCH$_3$ | CH$_2$Cl | N | |
| 128 | ⌇SO₂N— | H | OCH$_3$ | (cyclopropyl) | N | |
| 129 | ⌇SO₂N— | H | OCH$_3$ | CH(OCH$_3$)$_2$ | N | |
| 130 | ⌇SO₂N— | H | SCH$_3$ | CH$_3$ | N | |
| 131 | ⌇SO₂N— | H | SCH$_3$ | C$_2$H$_5$ | N | |
| 132 | ⌇SO₂N— | H | SCH$_3$ | OCH$_3$ | N | |
| 133 | ⌇SO₂N— | H | SCH$_3$ | OC$_2$H$_5$ | N | |
| 134 | ⌇SO₂N— | H | CH$_2$COOCH$_3$ | OCH$_3$ | N | |
| 135 | ⌇SO₂N— | H | CH$_2$COOCH$_3$ | OC$_2$H$_5$ | N | |

TABLE 1-continued
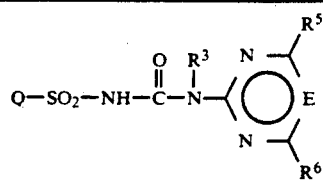
| Example | Q | $R^3$ | $R^5$ | $R^6$ | E | m.p. |
|---|---|---|---|---|---|---|
| 136 | ⌬SO₂N— | CH$_3$ | OCH$_3$ | OCH$_3$ | N | |
| 137 | ⌬SO₂N— | CH$_3$ | OCH$_3$ | CH$_3$ | N | |
| 138 | ⌬SO₂N— | C$_2$H$_5$ | OCH$_3$ | OCH$_3$ | N | |
| 139 | ⌬SO₂N— | C$_2$H$_5$ | OCH$_3$ | CH$_3$ | N | |
| 140 | ⌬SO₂N— | H | CF$_3$ | CH$_3$ | CH | |
| 141 | ⌬SO₂N— | H | CF$_3$ | OCH$_3$ | CH | |
| 142 | ⌬SO₂N— | H | CF$_3$ | OCH$_3$ | N | |
| 143 | CH$_3$-⌬SO₂N— | H | OCH$_3$ | OCH$_3$ | CH | 120–124 |
| 144 | CH$_3$-⌬SO₂N— | H | OCH$_3$ | CH$_3$ | CH | |
| 145 | CH$_3$-⌬SO₂N— | H | CH$_3$ | CH$_3$ | CH | |
| 146 | CH$_3$-⌬SO₂N— | H | OCH$_3$ | Cl | CH | |

TABLE 1-continued

Q—SO$_2$—NH—C(=O)—N(R$^3$)—[ring with N, N, E, R$^5$, R$^6$]

| Example | Q | R$^3$ | R$^5$ | R$^6$ | E | m.p. |
|---------|---|-------|-------|-------|---|------|
| 147 | CH$_3$-CH(-)-CH$_2$-CH$_2$-SO$_2$-N— (isothiazolidine 1,1-dioxide with CH$_3$) | H | OCH$_3$ | NHCH$_3$ | CH | |
| 148 | (same as 147) | H | OCHF$_2$ | OCH$_3$ | CH | |
| 149 | (same as 147) | H | OCHF$_2$ | OCHF$_2$ | CH | |
| 150 | (same as 147) | H | OCH$_3$ | OCH$_3$ | N | |
| 151 | (same as 147) | H | OCH$_3$ | CH$_3$ | N | |
| 152 | (same as 147) | CH$_3$ | OCH$_3$ | CH$_3$ | N | |
| 153 | (same as 147) | H | OCH$_3$ | NHCH$_3$ | N | |
| 154 | (same as 147) | H | OCH$_3$ | NHC$_2$H$_5$ | N | |
| 155 | CH$_3$ on other carbon, SO$_2$-N— ring | H | OCH$_3$ | OCH$_3$ | CH | |
| 156 | (same as 155) | H | OCH$_3$ | CH$_3$ | CH | |

TABLE 1-continued
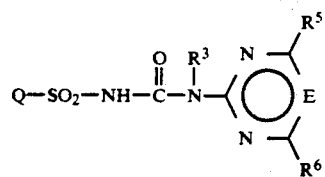
| Example | Q | $R^3$ | $R^5$ | $R^6$ | E | m.p. |
|---|---|---|---|---|---|---|
| 157 | CH₃—⟨SO₂/N—⟩ | H | CH₃ | CH₃ | CH | |
| 158 | CH₃—⟨SO₂/N—⟩ | H | OCH₃ | Cl | CH | |
| 159 | CH₃—⟨SO₂/N—⟩ | H | CH₃ | Cl | CH | |
| 160 | CH₃—⟨SO₂/N—⟩ | H | OCHF₂ | OCHF₂ | CH | |
| 161 | CH₃—⟨SO₂/N—⟩ | H | OCH₃ | CH₃ | N | |
| 162 | CH₃—⟨SO₂/N—⟩ | H | OCH₃ | OCH₃ | N | |
| 163 | CH₃—⟨SO₂/N—⟩ | CH₃ | OCH₃ | CH₃ | N | |
| 164 | ⟨SO₂/N—⟩CH₃ | H | OCH₃ | OCH₃ | CH | |
| 165 | ⟨SO₂/N—⟩CH₃ | H | OCH₃ | CH₃ | CH | |
| 166 | ⟨SO₂/N—⟩CH₃ | H | CH₃ | CH₃ | CH | |

TABLE 1-continued

Q—SO$_2$—NH—C(=O)—N(R$^3$)—[ring with R$^5$, R$^6$, E, N, N]

| Example | Q | R$^3$ | R$^5$ | R$^6$ | E | m.p. |
|---|---|---|---|---|---|---|
| 167 | (CH$_3$-CH-CH$_2$-CH$_2$-SO$_2$-N—) ring | H | OCH$_3$ | CH$_3$ | N | |
| 168 | (CH$_3$-CH-CH$_2$-CH$_2$-SO$_2$-N—) ring | H | OCH$_3$ | OCH$_3$ | N | |
| 169 | (CH$_3$-CH-CH$_2$-CH$_2$-SO$_2$-N—) ring | H | OCH$_3$ | Cl | CH | |
| 170 | (CH$_3$-CH-CH$_2$-CH$_2$-SO$_2$-N—) ring | H | OCH$_3$ | OCH$_2$CF$_3$ | CH | |
| 171 | (CH$_3$-CH-CH$_2$-CH$_2$-SO$_2$-N—) ring | H | OCH$_3$ | OCH$_2$CF$_3$ | N | |
| 172 | (CH$_3$,CH$_3$-disubstituted SO$_2$-N— ring) | H | OCH$_3$ | OCH$_3$ | CH | |
| 173 | (CH$_3$,CH$_3$-disubstituted SO$_2$-N— ring) | H | OCH$_3$ | CH$_3$ | CH | |
| 174 | (CH$_3$,CH$_3$-disubstituted SO$_2$-N— ring) | H | OCH$_3$ | CH$_3$ | N | |
| 175 | (CH$_3$,CH$_3$-disubstituted SO$_2$-N— ring) | CH$_3$ | OCH$_3$ | CH$_3$ | CH | |

TABLE 1-continued
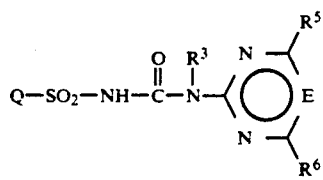
| Example | Q | $R^3$ | $R^5$ | $R^6$ | E | m.p. |
|---|---|---|---|---|---|---|
| 176 | CH₃–CH(–SO₂–N–)–CH(CH₃) (ring) | H | OCH₃ | OCH₃ | CH | |
| 177 | CH₃–CH(–SO₂–N–)–CH(CH₃) (ring) | H | CH₃ | CH₃ | CH | |
| 178 | CH₃–CH(–SO₂–N–)–CH(CH₃) (ring) | H | OCH₃ | OCH₃ | N | |
| 179 | CH₃–CH(–SO₂–N–)–CH(CH₃) (ring) | H | OCH₃ | CH₃ | N | |
| 180 | CH₃–CH(CH₃)–CH(–SO₂–N–) (ring) | H | OCH₃ | OCH₃ | CH | |
| 181 | CH₃–CH(CH₃)–CH(–SO₂–N–) (ring) | H | OCH₃ | CH₃ | CH | |
| 182 | CH₃–CH(CH₃)–CH(–SO₂–N–) (ring) | H | OCH₃ | Cl | CH | |
| 183 | CH₃–CH(CH₃)–CH(–SO₂–N–) (ring) | H | OCH₃ | cyclopropyl | N | |

TABLE 1-continued $$Q-SO_2-NH-\overset{O}{\underset{}{C}}-\underset{}{\overset{R^3}{N}}-\underset{N}{\overset{N}{\diagup}}\overset{R^5}{\underset{R^6}{\diagdown}}E$$

| Example | Q | $R^3$ | $R^5$ | $R^6$ | E | m.p. |
|---|---|---|---|---|---|---|
| 184 | CH$_3$OOC–(CH$_2$)$_2$–SO$_2$–N— | H | OCH$_3$ | OCH$_3$ | CH | |
| 185 | CH$_3$OOC–(CH$_2$)$_2$–SO$_2$–N— | H | OCH$_3$ | OCH$_3$ | N | |
| 186 | CH$_3$OOC–(CH$_2$)$_2$–SO$_2$–N— | H | OCH$_3$ | Cl | CH | |
| 187 | C$_2$H$_5$OOC–(CH$_2$)$_2$–SO$_2$–N— | H | OCH$_3$ | OCH$_3$ | CH | |
| 188 | C$_2$H$_5$OOC–(CH$_2$)$_2$–SO$_2$–N— | H | CH$_3$ | CH$_3$ | CH | |
| 189 | C$_2$H$_5$OOC–(CH$_2$)$_2$–SO$_2$–N— | H | CH$_3$ | cyclopropyl | CH | |
| 190 | C$_3$H$_7$OOC–(CH$_2$)$_2$–SO$_2$–N— | H | OCH$_3$ | OCH$_3$ | CH | |
| 191 | C$_7$H$_9$OOC–(CH$_2$)$_2$–SO$_2$–N— | H | OCH$_3$ | OCH$_3$ | CH | |
| 192 | CH$_3$OOC–CH–CH$_2$–SO$_2$–N— | H | OCH$_3$ | OCH$_3$ | CH | |
| 193 | CH$_3$OOC–CH–CH$_2$–SO$_2$–N— | H | CH$_3$ | CH$_3$ | CH | |

TABLE 1-continued
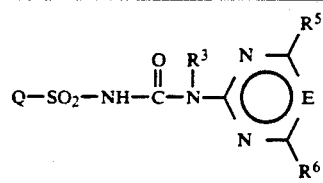
| Example | Q | $R^3$ | $R^5$ | $R^6$ | E | m.p. |
|---|---|---|---|---|---|---|
| 194 | CH3OOC—[ring with SO2, N—] | H | OCH3 | Cl | CH | |
| 195 | CH3OOC—[ring with SO2, N—] | H | OCH3 | CH3 | N | |
| 196 | Cl—[ring with SO2, N—] | H | OCH3 | OCH3 | CH | |
| 197 | Cl—[ring with SO2, N—] | H | OCH3 | CH3 | CH | |
| 198 | Cl—[ring with SO2, N—] | H | OCH3 | Cl | CH | |
| 199 | Cl—[ring with SO2, N—] | H | OCH3 | CH3 | N | |
| 200 | Cl—[ring with SO2, N—] | H | OCH3 | OCH3 | CH | |
| 201 | Cl—[ring with SO2, N—] | H | OCH3 | CH3 | N | |
| 202 | Cl, CH3—[ring with SO2, N—] | H | OCH3 | OCH3 | CH | |
| 203 | Cl—[ring with SO2, N—]—CH3 | H | OCH3 | OCH3 | CH | |

TABLE 1-continued $$Q-SO_2-NH-\overset{\overset{\displaystyle O}{\|}}{C}-\underset{R^3}{N}-\underset{\underset{\displaystyle N}{\|}}{\overset{\overset{\displaystyle N}{\|}}{\bigcirc}}\overset{\displaystyle R^5}{\underset{\displaystyle R^6}{E}}$$

| Example | Q | $R^3$ | $R^5$ | $R^6$ | E | m.p. |
|---|---|---|---|---|---|---|
| 204 | [3-chloro-isothiazolidine-1,1-dioxide, N-linked] | H | $OCH_3$ | $OCH_3$ | CH | |
| 205 | [3,4-dichloro-isothiazolidine-1,1-dioxide, N-linked] | H | $OCH_3$ | $OCH_3$ | CH | |
| 206 | [3-bromo-isothiazolidine-1,1-dioxide, N-linked] | H | $OCH_3$ | $OCH_3$ | CH | |
| 207 | [3-bromo-isothiazolidine-1,1-dioxide, N-linked] | H | $OCH_3$ | $CH_3$ | N | |
| 208 | [2,3-dihydroisothiazole-1,1-dioxide, N-linked] | H | $OCH_3$ | $OCH_3$ | CH | |
| 209 | [2,3-dihydroisothiazole-1,1-dioxide, N-linked] | H | $OCH_3$ | Cl | CH | |
| 210 | [2,3-dihydroisothiazole-1,1-dioxide, N-linked] | H | $OCH_3$ | $CH_3$ | N | |
| 211 | [2,5-dihydroisothiazole-1,1-dioxide, N-linked] | H | $OCH_3$ | $OCH_3$ | CH | |
| 212 | [2,5-dihydroisothiazole-1,1-dioxide, N-linked] | H | $OCH_3$ | Cl | CH | |
| 213 | [2,5-dihydroisothiazole-1,1-dioxide, N-linked] | H | $OCH_3$ | $NHCH_3$ | N | |
| 214 | [3-chloro-isothiazolidine-1,1-dioxide, N-linked] | H | $OCH_3$ | $OCH_3$ | CH | |

TABLE 1-continued
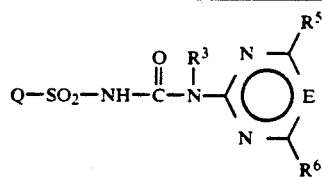
| Example | Q | R³ | R⁵ | R⁶ | E | m.p. |
|---|---|---|---|---|---|---|
| 215 | Cl-CH(CH₂)-SO₂-N— (5-ring, Cl on ring) | H | OCH₃ | CH₃ | N | |
| 216 | Cl-CH(CH₂)-SO₂-N— | H | OCH₃ | OCH₃ | CH | |
| 217 | Cl-CH-CH₂-SO₂-N— | H | OCH₃ | CH₃ | N | |
| 218 | Cl-CH(CH₂)₂-SO₂-N— | H | OCH₃ | OCH₃ | CH | |
| 219 | Cl-CH(CH₂)₂-SO₂-N— | H | OCH₃ | CH₃ | N | |
| 220 | (6-ring)-SO₂-N— | H | OCH₃ | CH₃ | CH | 172–173 |
| 221 | (6-ring)-SO₂-N— | H | OCH₃ | CH₃ | CH | 162–164 |
| 222 | (6-ring)-SO₂-N— | H | OCH₃ | Cl | CH | 148–149 |
| 223 | (6-ring)-SO₂-N— | H | CH₃ | Cl | CH | |
| 224 | (6-ring)-SO₂-N— | H | CH₃ | Br | CH | |
| 225 | (6-ring)-SO₂-N— | H | OCH₃ | Br | CH | |

TABLE 1-continued $$Q-SO_2-NH-\overset{O}{\underset{}{C}}-\underset{R^3}{N}-\underset{N}{\overset{N}{\diagdown}}\underset{R^6}{\overset{R^5}{\diagup}}E$$

| Example | Q | $R^3$ | $R^5$ | $R^6$ | E | m.p. |
|---------|---|-------|-------|-------|---|------|
| 226 | piperidine-SO₂-N— | H | $OCHF_2$ | $OCHF_2$ | CH | |
| 227 | piperidine-SO₂-N— | H | $OCHF_2$ | $OCH_3$ | CH | |
| 228 | piperidine-SO₂-N— | H | $OCH_3$ | $OCH_2CF_3$ | CH | |
| 229 | piperidine-SO₂-N— | H | $OC_2H_5$ | $OCH_2CF_3$ | CH | |
| 230 | piperidine-SO₂-N— | H | $OC_2H_5$ | $OC_2H_5$ | CH | |
| 231 | piperidine-SO₂-N— | H | $SCH_3$ | $CH_3$ | CH | |
| 232 | piperidine-SO₂-N— | H | $OCH_3$ | $NHCH_3$ | CH | |
| 233 | piperidine-SO₂-N— | H | $CH_3$ | $N(CH_3)_2$ | CH | |
| 234 | piperidine-SO₂-N— | H | $OCH_3$ | cyclopropyl | CH | |
| 235 | piperidine-SO₂-N— | H | $CH_3$ | cyclopropyl | CH | |
| 236 | piperidine-SO₂-N— | H | $OCHF_2$ | $OCHF_2$ | CH | |
| 237 | piperidine-SO₂-N— | $CH_3$ | $OCH_3$ | $OCH_3$ | CH | |

TABLE 1-continued

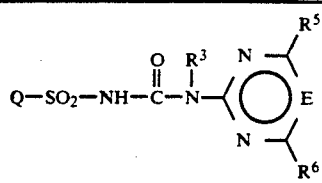

| Example | Q | R³ | R⁵ | R⁶ | E | m.p. |
|---|---|---|---|---|---|---|
| 238 | piperidine-SO₂-N— | CH₃ | CH₃ | CH₃ | CH | |
| 239 | piperidine-SO₂-N— | H | OCH₃ | OCH₃ | N | |
| 240 | piperidine-SO₂-N— | H | OCH₃ | CH₃ | N | |
| 241 | piperidine-SO₂-N— | H | OCH₃ | SCH₃ | N | |
| 242 | piperidine-SO₂-N— | H | CH₃ | CH₃ | N | |
| 243 | piperidine-SO₂-N— | H | OC₂H₅ | OCH₃ | N | |
| 244 | piperidine-SO₂-N— | H | OCH₃ | NHCH₃ | N | |
| 245 | piperidine-SO₂-N— | H | OC₂H₅ | NHCH₃ | N | |
| 246 | piperidine-SO₂-N— | H | OCH₃ | NHC₂H₅ | N | |
| 247 | piperidine-SO₂-N— | H | OC₂H₅ | NHC₂H₅ | N | |
| 248 | piperidine-SO₂-N— | H | OCH₃ | N(CH₃)₂ | N | |
| 249 | piperidine-SO₂-N— | H | OC₂H₅ | N(CH₃)₂ | N | |

TABLE 1-continued $$Q-SO_2-NH-\overset{O}{\overset{\|}{C}}-\overset{R^3}{\underset{}{N}}-\text{[ring with N, E, N, R}^5\text{, R}^6\text{]}$$

| Example | Q | R³ | R⁵ | R⁶ | E | m.p. |
|---------|---|-----|-----|-----|---|------|
| 250 | cyclohexyl-SO₂-N— | H | OCH₃ | — | N | |
| 251 | cyclohexyl-SO₂-N— | H | OCH₃ | OCH₂CF₃ | N | |
| 252 | cyclohexyl-SO₂-N— | H | CH₃ | OCH₂CF₃ | N | |
| 253 | cyclohexyl-SO₂-N— | CH₃ | OCH₃ | CH₃ | N | |
| 254 | cyclohexyl-SO₂-N— | CH₃ | OCH₃ | OCH₃ | N | |
| 255 | cyclohexyl-SO₂-N— | CH₃ | OCH₃ | NHCH₃ | N | |
| 256 | cyclohexenyl-SO₂-N— | H | OCH₃ | OCH₃ | CH | 48–50 |
| 257 | cyclohexenyl-SO₂-N— | H | OCH₃ | CH₃ | CH | |
| 258 | cyclohexenyl-SO₂-N— | H | CH₃ | CH₃ | CH | |
| 259 | cyclohexenyl-SO₂-N— | H | OCH₃ | Cl | CH | |
| 260 | cyclohexenyl-SO₂-N— | H | OCH₃ | Br | CH | |
| 261 | cyclohexenyl-SO₂-N— | H | OC₂H₅ | OCH₃ | CH | |

TABLE 1-continued

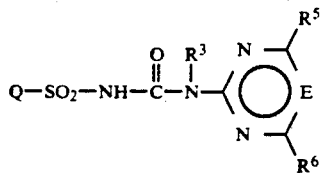

| Example | Q | R³ | R⁵ | R⁶ | E | m.p. |
|---|---|---|---|---|---|---|
| 262 | (cyclohexenyl-SO₂-N—) | H | OC₂H₅ | OC₂H₅ | CH | |
| 263 | (cyclohexenyl-SO₂-N—) | H | OCH₃ | NHCH₃ | CH | |
| 264 | (cyclohexenyl-SO₂-N—) | H | OCH₃ | CH₃ | N | |
| 265 | (cyclohexenyl-SO₂-N—) | H | OCH₃ | NHCH₃ | N | |
| 266 | (cyclohexenyl-SO₂-N—) | CH₃ | OCH₃ | CH₃ | N | |
| 267 | (cyclohexenyl-SO₂-N—) | H | OCH₃ | OCH₂CF₃ | CH | |
| 268 | (cyclohexenyl-SO₂-N—) | H | OCH₃ | OCH₃ | CH | |
| 269 | (cyclohexenyl-SO₂-N—) | H | OCH₃ | CH₃ | CH | |
| 270 | (cyclohexenyl-SO₂-N—) | H | CH₃ | CH₃ | CH | |
| 271 | (cyclohexenyl-SO₂-N—) | H | OCH₃ | Cl | CH | |
| 272 | (cyclohexenyl-SO₂-N—) | H | CH₃ | Cl | CH | |
| 273 | (cyclohexenyl-SO₂-N—) | H | OCH₃ | OCH₂CF₃ | CH | |

TABLE 1-continued

Structure: Q—SO$_2$—NH—C(=O)—N(R$^3$)—[pyrimidine/triazine ring with R$^5$, R$^6$, E]

| Example | Q | R$^3$ | R$^5$ | R$^6$ | E | m.p. |
|---|---|---|---|---|---|---|
| 274 | cyclohexene-SO$_2$-N— | H | OCHF$_2$ | OCHF$_2$ | CH | |
| 275 | cyclohexene-SO$_2$-N— | H | OCH$_3$ | CH$_3$ | N | |
| 276 | cyclohexene-SO$_2$-N— | CH$_3$ | OCH$_3$ | CH$_3$ | N | |
| 277 | cyclohexene-SO$_2$-N— | H | OH$_3$ | cyclopropyl | N | |
| 278 | cyclohexene-SO$_2$-N— | H | OC$_2$H$_5$ | NHCH$_3$ | N | |
| 279 | cyclohexene-SO$_2$-N— | H | SCH$_3$ | CH$_3$ | N | |
| 280 | cyclohexene-SO$_2$-N— | H | OCH$_3$ | OCH$_3$ | CH | |
| 281 | cyclohexene-SO$_2$-N— | H | OCH$_3$ | CH$_3$ | CH | |
| 282 | cyclohexene-SO$_2$-N— | H | CH$_3$ | CH$_3$ | CH | |
| 283 | cyclohexene-SO$_2$-N— | H | OCH$_3$ | Cl | CH | |
| 284 | cyclohexene-SO$_2$-N— | H | OCHF$_2$ | OCHF$_2$ | CH | |
| 285 | cyclohexene-SO$_2$-N— | H | SCH$_3$ | CH$_3$ | CH | |

TABLE 1-continued $$Q-SO_2-NH-\overset{O}{\underset{}{C}}-\overset{R^3}{\underset{}{N}}-\underset{N}{\overset{N}{\diagup}}\overset{R^5}{\underset{R^6}{\diagdown}}E$$

| Example | Q | $R^3$ | $R^5$ | $R^6$ | E | m.p. |
|---------|---|-------|-------|-------|---|------|
| 286 | cyclohexenyl-SO$_2$-N- | H | OC$_2$H$_5$ | NHCH$_3$ | CH | |
| 287 | cyclohexenyl-SO$_2$-N- | H | OCH$_3$ | CH$_3$ | N | |
| 288 | cyclohexenyl-SO$_2$-N- | CH$_3$ | OCH$_3$ | CH$_3$ | N | |
| 289 | cyclohexenyl-SO$_2$-N- | H | OCH$_3$ | OCH$_3$ | N | |
| 290 | cyclohexenyl-SO$_2$-N- | H | OCH$_3$ | OCH$_2$CF$_3$ | N | |
| 291 | cyclohexenyl-SO$_2$-N- | H | OCH$_3$ | cyclopropyl | N | |
| 292 | cyclohexenyl-SO$_2$-N- | H | OCH$_3$ | OCH$_3$ | CH | |
| 293 | cyclohexenyl-SO$_2$-N- | H | OCH$_3$ | CH$_3$ | CH | |
| 294 | cyclohexenyl-SO$_2$-N- | H | CH$_3$ | CH$_3$ | CH | |
| 295 | cyclohexenyl-SO$_2$-N- | H | OCH$_3$ | Cl | CH | |
| 296 | cyclohexenyl-SO$_2$-N- | H | OCHF$_2$ | OCHF$_2$ | CH | |
| 297 | cyclohexenyl-SO$_2$-N- | H | OCHF$_2$ | OCH$_3$ | CH | |

TABLE 1-continued $$Q-SO_2-NH-\overset{O}{\underset{}{C}}-\underset{R^3}{N}-\underset{R^6}{\overset{R^5}{\underset{N}{\bigcirc}}}E$$

| Example | Q | $R^3$ | $R^5$ | $R^6$ | E | m.p. |
|---|---|---|---|---|---|---|
| 298 | (2H-thiazine-SO2-N-) | H | $OCHF_2$ | $CH_3$ | CH | |
| 299 | (2H-thiazine-SO2-N-) | H | $OCH_3$ | $CH_3$ | N | |
| 300 | (2H-thiazine-SO2-N-) | $CH_3$ | $OCH_3$ | $CH_3$ | N | |
| 301 | (2H-thiazine-SO2-N-) | H | $OCH_3$ | $OCH_3$ | N | |
| 302 | (2H-thiazine-SO2-N-) | H | $CH_3$ | $CH_3$ | N | |
| 303 | (2H-thiazine-SO2-N-) | N | H | $CH_3$ | CH | |
| 304 | (3,5-diMe-2H-thiazine-SO2-N-) | H | $OCH_3$ | $OCH_3$ | CH | |
| 305 | (3,5-diMe-2H-thiazine-SO2-N-) | H | $OCH_3$ | $CH_3$ | N | |
| 306 | (3,5-diMe-2H-thiazine-SO2-N-) | H | $OCH_3$ | $OCH_3$ | CH | 112–114 |
| 307 | (3,5-diMe-2H-thiazine-SO2-N-) | H | $OCH_3$ | $CH_3$ | CH | |

TABLE 1-continued
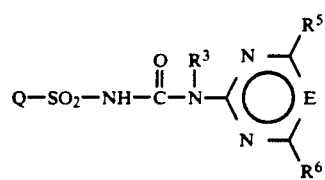
| Example | Q | R³ | R⁵ | R⁶ | E | m.p. |
|---|---|---|---|---|---|---|
| 308 | CH₃-/SO₂-N-/CH₃ | H | CH₃ | CH₃ | CH | |
| 309 | CH₃-/SO₂-N-/CH₃ | H | OCH₃ | Cl | CH | |
| 310 | CH₃-/SO₂-N-/CH₃ | H | OCHF₂ | OCHF₂ | CH | |
| 311 | CH₃-/SO₂-N-/CH₃ | H | OCH₃ | NHCH₃ | CH | |
| 312 | CH₃-/SO₂-N-/CH₃ | H | OCH₃ | CH₃ | N | |
| 313 | Cl, CH₃-/SO₂-N-/CH₃ | CH₃ | OCH₃ | CH₃ | N | |
| 314 | Cl, CH₃-/SO₂-N-/CH₃ | H | OCH₃ | OCH₃ | N | |
| 315 | Br, CH₃-/SO₂-N-/CH₃ | H | CH₃ | CH₃ | N | |

TABLE 1-continued $$Q-SO_2-NH-\overset{O}{\underset{}{C}}-\underset{R^3}{N}-\underset{N}{\overset{N}{\bigcirc}}\overset{R^5}{\underset{R^6}{E}}$$

| Example | Q | R³ | R⁵ | R⁶ | E | m.p. |
|---------|---|-----|-----|-----|-----|------|
| 316 | Cl-CH(CH₂)₃-SO₂-N— (Cl on ring position) | H | OCH₃ | OCH₃ | CH | |
| 317 | Cl-CH(CH₂)₃-SO₂-N— | H | OCH₃ | CL | CH | |
| 318 | Cl-CH(CH₂)₃-SO₂-N— | H | OCH₃ | CH₃ | CH | |
| 319 | Cl-CH(CH₂)₃-SO₂-N— | H | CH₃ | CH₃ | CH | |
| 320 | Cl-ring-SO₂-N— | H | OCH₃ | OCH₃ | CH | |
| 321 | Cl-ring-SO₂-N— | H | CH₃ | CH₃ | CH | |
| 322 | Cl-ring-SO₂-N— | H | OCH₃ | NHCH₃ | CH | |
| 323 | Cl-ring-SO₂-N— | H | CH₃ | H | CH | |
| 324 | Cl-ring-SO₂-N— | H | OCH₃ | OCH₃ | CH | |
| 325 | Cl-ring-SO₂-N— | CH₃ | OCH₃ | CH₃ | N | |
| 326 | Cl-ring-SO₂-N— | H | OCH₃ | OCH₃ | N | |

TABLE 1-continued

Q—SO$_2$—NH—C(=O)—N(R$^3$)—[ring with R$^5$, R$^6$, E]

| Example | Q | R$^3$ | R$^5$ | R$^6$ | E | m.p. |
|---|---|---|---|---|---|---|
| 327 | 3-chloro-sulfolanyl-N— | H | OCH$_3$ | — | N | |
| 328 | 3-chloro-2,3-dihydrothiophene-1,1-dioxide-N— | H | OCH$_3$ | CH$_3$ | CH | |
| 329 | 3-chloro-2,3-dihydrothiophene-1,1-dioxide-N— | H | OCH$_3$ | CH$_3$ | CH | |
| 330 | 3-chloro-2,3-dihydrothiophene-1,1-dioxide-N— | H | OCH$_3$ | H | CH | |
| 331 | 4-chloro-2,3-dihydrothiophene-1,1-dioxide-N— | H | OCH$_3$ | OCH$_3$ | CH | |
| 332 | 4-chloro-2,3-dihydrothiophene-1,1-dioxide-N— | H | OCH$_3$ | CH$_3$ | N | |
| 333 | 4-chloro-2,3-dihydrothiophene-1,1-dioxide-N— | H | OCH$_3$ | H | N | |
| 334 | 4-chloro-2,3-dihydrothiophene-1,1-dioxide-N— | H | OCH$_3$ | OCH$_3$ | CH | |
| 335 | 4-chloro-2,3-dihydrothiophene-1,1-dioxide-N— | H | OCHF$_2$ | OCHF$_2$ | CH | |
| 336 | 4-chloro-2,3-dihydrothiophene-1,1-dioxide-N— | H | CH$_3$ | CH$_3$ | CH | |
| 337 | 4-chloro-2,3-dihydrothiophene-1,1-dioxide-N— | H | OCH$_3$ | OCH$_3$ | CH | |

TABLE 1-continued

Q—SO$_2$—NH—C(=O)—N(R$^3$)—[ring with R$^5$, R$^6$, E, N, N]

| Example | Q | R$^3$ | R$^5$ | R$^6$ | E | m.p. |
|---------|---|-------|-------|-------|---|------|
| 338 | 3-chloro-2,5-dihydrothiazine-1,1-dioxide (Cl on vinyl, SO$_2$-N-CH$_2$-CH=CCl-CH$_2$) | H | SCH$_3$ | CH$_3$ | CH | |
| 339 | same as 338 | H | OCH$_3$ | CH$_3$ | N | |
| 340 | 6-chloro-3,6-dihydro-2H-1,2-thiazine 1,1-dioxide | H | OCH$_3$ | OCH$_3$ | CH | |
| 341 | same as 340 | H | CH$_3$ | CH$_3$ | CH | |
| 342 | same as 340 | H | OCH$_3$ | CH$_3$ | N | |
| 343 | 5-chloro-3,6-dihydro-2H-1,2-thiazine 1,1-dioxide | H | OCH$_3$ | OCH$_3$ | CH | |
| 344 | same as 343 | H | CH$_3$ | CH$_3$ | CH | |
| 345 | same as 343 | H | OCH$_3$ | CH$_3$ | N | |
| 346 | 3-(methoxycarbonyl)-tetrahydro-2H-1,2-thiazine 1,1-dioxide | H | OCH$_3$ | OCH$_3$ | CH | |
| 347 | same as 346 | H | CH$_3$ | CH$_3$ | CH | |

TABLE 1-continued

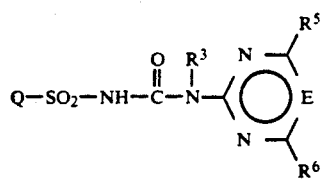

| Example | Q | $R^3$ | $R^5$ | $R^6$ | E | m.p. |
|---|---|---|---|---|---|---|
| 348 | (COOC$_2$H$_5$, SO$_2$-N-piperidinyl) | H | OCH$_3$ | OCH$_3$ | CH | |
| 349 | (CH$_3$OOC, SO$_2$-N-piperidinyl) | H | OCH$_3$ | OCH$_3$ | CH | |
| 350 | (CH$_3$OOC, SO$_2$-N-piperidinyl) | H | CH$_3$ | CH$_3$ | CH | |
| 351 | (CH$_3$OOC, SO$_2$-N-piperidinyl) | H | OCH$_3$ | CH$_3$ | N | |
| 352 | (CH$_3$OOC, SO$_2$-N-piperidinyl) | H | OCH$_3$ | OCH$_3$ | CH | |
| 353 | (CH$_3$OOC, SO$_2$-N-piperidinyl) | H | OCH$_3$ | Cl | CH | |
| 354 | (C$_2$H$_5$OOC, SO$_2$-N-piperidinyl) | H | OCH$_3$ | OCH$_3$ | CH | |
| 355 | (CH$_3$OOC, SO$_2$-N-piperidinyl) | H | OCH$_3$ | OCH$_3$ | CH | |
| 356 | (CH$_3$OOC, SO$_2$-N-piperidinyl) | H | OCH$_3$ | CH$_3$ | N | |
| 357 | (CH$_3$OOC, SO$_2$-N-piperidinyl) | CH$_3$ | OCH$_3$ | CH$_3$ | N | |

TABLE 1-continued $$Q-SO_2-NH-\overset{O}{\underset{\parallel}{C}}-\underset{R^3}{N}-\underset{\underset{R^6}{\overset{N}{\diagdown}}}{\overset{\underset{R^5}{\overset{N}{\diagup}}}{\diagup}}E$$

| Example | Q | $R^3$ | $R^5$ | $R^6$ | E | m.p. |
|---|---|---|---|---|---|---|
| 358 | COOCH₃ cyclic with SO₂-N— | H | OCH₃ | OCH₃ | CH | |
| 359 | COOCH₃ cyclic with SO₂-N— | H | OCH₃ | CH₃ | N | |
| 360 | COOC₂H₅ cyclic with SO₂-N— | H | OCH₃ | OCH₃ | CH | |
| 361 | CH₃OOC— cyclic with SO₂-N— | H | OCH₃ | OCH₃ | CH | |
| 362 | CH₃OOC— cyclic with SO₂-N— | H | OCH₃ | CH₃ | N | |
| 363 | CH₃OOC— cyclic with SO₂-N— | CH₃ | OCH₃ | OCH₃ | CH | |
| 364 | CH₃OOC— cyclic with SO₂-N— | H | OCH₃ | OCH₃ | CH | |
| 365 | CH₃OOC— cyclic with SO₂-N— | H | OCH₃ | Cl | CH | |
| 366 | CH₃OOC— cyclic with SO₂-N— | H | OCH₃ | CH₃ | N | |
| 367 | CH₃OOC— cyclic with SO₂-N— | H | OCH₃ | OCH₃ | CH | |

TABLE 1-continued

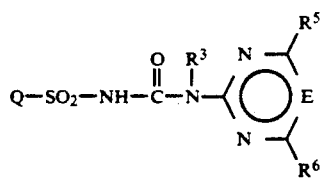

| Example | Q | R³ | R⁵ | R⁶ | E | m.p. |
|---|---|---|---|---|---|---|
| 368 | ![](SO2-N ring with CH3OOC, CH=CH) | H | OCH₃ | CH₃ | N | |
| 369 | ![](SO2-N ring with CH3OOC) | H | OCH₃ | Cl | CH | |
| 370 | ![](SO2-N ring with C2H5OOC) | H | OCH₃ | OCH₃ | CH | |
| 371 | ![](SO2-N ring with C2H5OOC) | H | OCH₃ | CH₃ | N | |
| 372 | ![](CH3 substituted SO2-N ring) | H | OCH₃ | OCH₃ | CH | |
| 373 | ![](CH3 substituted SO2-N ring) | H | OCH₃ | CH₃ | N | |
| 374 | ![](CH3 substituted SO2-N ring) | CH₃ | OCH₃ | CH₃ | N | |
| 375 | ![](CH3 substituted SO2-N ring) | H | OCH₃ | Cl | CH | |
| 376 | ![](CH3 substituted SO2-N ring) | H | OCH₃ | OCH₃ | CH | |
| 377 | ![](CH3 substituted SO2-N ring) | H | OCH₃ | Cl | CH | |

TABLE 1-continued

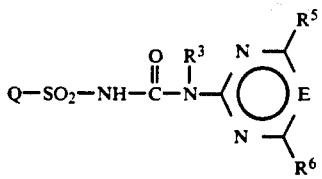

| Example | Q | $R^3$ | $R^5$ | $R^6$ | E | m.p. |
|---|---|---|---|---|---|---|
| 378 | CH₃-cyclohexenyl-CH₂-SO₂-N— | H | $CH_3$ | $CH_3$ | CH | |
| 379 | CH₃-cyclohexenyl-CH₂-SO₂-N— | H | $OCH_3$ | $CH_3$ | N | |
| 380 | (CH₃)₂-cyclohexenyl-SO₂-N— | H | $OCH_3$ | $OCH_3$ | CH | |
| 381 | (CH₃)₂-cyclohexenyl-SO₂-N— | H | $OCH_3$ | $CH_3$ | CH | |
| 382 | (CH₃)₂-cyclohexenyl-SO₂-N— | H | $OCH_3$ | Cl | CH | |
| 383 | (CH₃)₂-cyclohexenyl-SO₂-N— | H | $OCHF_2$ | $OCHF_2$ | CH | |
| 384 | (CH₃)₂-cyclohexenyl-SO₂-N— | H | $OCH_3$ | $CH_3$ | N | |
| 385 | (CH₃)₂-cyclohexenyl-SO₂-N— | $CH_3$ | $OCH_3$ | $CH_3$ | N | |
| 386 | (CH₃)₂-cyclohexenyl-SO₂-N— | H | $OCH_3$ | $NHCH_3$ | N | |
| 387 | (CH₃)₂-cyclohexenyl-SO₂-N— | H | $OCH_3$ | $OCH_2CF_3$ | N | |
| 388 | CH₃-cyclohexenyl-SO₂-N— | H | $OCH_3$ | $OCH_3$ | CH | |

TABLE 1-continued
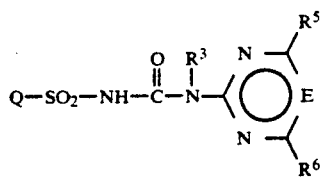
| Example | Q | R³ | R⁵ | R⁶ | E | m.p. |
|---|---|---|---|---|---|---|
| 389 | CH₃–[ring with SO₂–N–] | CH₃ | OCH₃ | OCH₃ | CH | |
| 390 | CH₃–[ring with SO₂–N–] | H | OCH₃ | CH₃ | N | |
| 391 | [ring with SO₂–N–, CH₃] | H | OCH₃ | OCH₃ | CH | |
| 392 | [ring with SO₂–N–, CH₃] | H | OCH₃ | Cl | CH | |
| 393 | [ring with SO₂–N–, CH₃] | H | CH₃ | CH₃ | CH | |
| 394 | [ring with SO₂–N–, CH₃] | H | OCH₃ | CH₃ | N | |
| 395 | CH₃–[ring with SO₂–N–, CH₃] | H | OCH₃ | OCH₃ | CH | |
| 396 | CH₃–[ring with SO₂–N–, CH₃] | H | OCH₃ | CH₃ | CH | |

TABLE 1-continued

Structure: Q—SO$_2$—NH—C(=O)—N(R$^3$)—[ring with R$^5$, E, R$^6$, two N]

| Example | Q | R$^3$ | R$^5$ | R$^6$ | E | m.p. |
|---|---|---|---|---|---|---|
| 397 | CH$_3$-CH(—SO$_2$—N—)—CH=CH—CH(CH$_3$)— (ring) | H | CH$_3$ | CH$_3$ | CH | |
| 398 | (same ring as 397) | H | OCH$_3$ | Cl | CH | |
| 399 | (same ring as 397) | H | OCH$_3$ | CH$_3$ | N | |

TABLE 2

Structure: Q—SO$_2$—NH—C(=S)—N(R$^3$)—[ring with R$^5$, E, R$^6$, two N]

| Example | Q | R$^3$ | R$^5$ | R$^6$ | E | m.p. |
|---|---|---|---|---|---|---|
| 400 | 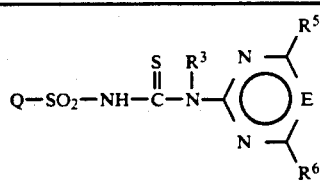 (SO$_2$–N ring, small) | H | OCH$_3$ | OCH$_3$ | CH | |
| 401 | (SO$_2$–N 5-membered ring) | H | OCH$_3$ | OCH$_3$ | CH | |
| 402 | CH$_3$-substituted SO$_2$–N 5-ring | H | OCH$_3$ | OCH$_3$ | CH | |
| 403 | CH$_3$-substituted SO$_2$–N 5-ring | H | OCH$_3$ | CH$_3$ | N | |
| 404 | SO$_2$–N 6-membered ring | H | OCH$_3$ | OCH$_3$ | CH | |

TABLE 2-continued

| Example | Q | R$^3$ | R$^5$ | R$^6$ | E | m.p. |
|---|---|---|---|---|---|---|
| 405 | 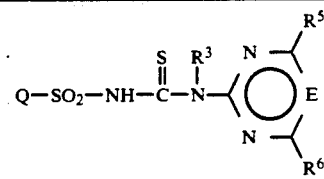 (SO$_2$–N 6-ring) | H | OCH$_3$ | CH$_3$ | N | |
| 406 | SO$_2$–N 6-ring with double bond | H | OCH$_3$ | OCH$_3$ | CH | |
| 407 | SO$_2$–N 6-ring with double bond | H | OCH$_3$ | Cl | CH | |
| 408 | SO$_2$–N 6-ring with double bond | H | OCH$_3$ | OCH$_3$ | CH | |
| 409 | CH$_3$, CH$_3$ disubstituted SO$_2$–N 6-ring with double bonds | H | OCH$_3$ | OCH$_3$ | CH | |

TABLE 2-continued

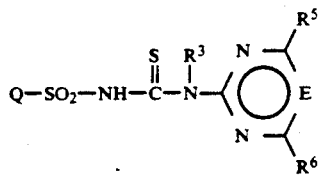

| Example | Q | R³ | R⁵ | R⁶ | E | m.p. |
|---------|---|----|----|----|---|------|
| 410 | CH₃-[ring]-SO₂-N(CH₃)- | H | CH₃ | CH₃ | CH | |
| 411 | CH₃-[ring]-SO₂-N(CH₃)- | H | OCH₃ | OCH₃ | N | |

BIOLOGICAL EXAMPLES

The damage to the weeds and the tolerance by crop plants were scored according to a key where numbers from 0 to 5 express the activity. In this key:
0 denotes no action
1 denotes 0-20% action or damage
2 denotes 20-40% action or damage
3 denotes 40-60% action or damage
4 denotes 60-80% action or damage
5 denotes 80-100% action or damage

1. Pre-emergence action on weeds

Seeds or rhizome pieces of monocotyledon and dicotyledon weeds were placed in plastic pots containing sandy loam and covered with soil. Various dosages of aqueous suspensions or emulsions of the compounds according to the invention formulated as wettable powders or emulsion concentrates were then applied to the surface of the cover soil, applying about 600-800 l/ha of water.

After treatment, the pots were placed in the greenhouse and kept under good growth conditions for the weeds. Visual scoring of the plant damage or the emergence damage was carried out after emergence of the test plants after a trial period of 3-4 weeks, comparing them to untreated control plants. As shown by the score data in Table 2, the compounds according to the invention have a good herbicidal pre-emergence activity against a broad range of weed grasses and weeds.

2. Post-emergence action on weeds

Seeds or rhizome pieces of monocotyledon and dicotyledon weeds were placed in plastic pots in sandy loam, covered with soil and grown in the greenhouse under good growth conditions. Three weeks after sowing, the test plants were treated in the three-leaf stage.

Various dosages of the compounds according to the invention formulated as wettable powders or emulsion concentrates were sprayed onto the green parts of the plants, applying about 600-800 l/ha of water, and the action of the preparations was scored visually after the test plants had remained in the greenhouse for about 3 to 4 weeks under optimum growth conditions, comparing them to untreated control plants.

The agents according to the invention also exhibit a good herbicidal activity against a broad range of economically important weed grasses and weeds in the post-emergence treatment (Table 3).

3. Tolerance by crop plants

In further greenhouse experiments, seeds of a relatively large number of crop plants and weeds were placed in sandy loam and covered with soil.

Some of the pots were treated immediately as described under 1., and the remainder was placed in the greenhouse until the plants had developed two to three true leaves and were then sprayed with various dosages of the substances according to the invention as described under 2.

Four to five weeks after application, with the plants remaining in the greenhouse, visual scoring revealed that the compounds according to the invention did not cause any damage to dicotyledon crops, such as, for example soya beans, cotton, oilseed rape, sugar beet and potatoes when applied either as a pre-emergence and post-emergence treatment, even at high dosages of active substance. Furthermore, some of the substances also left crops of the Gramineae such as, for example barley, wheat, rye, sorghum millet species, maize or rice, unaffected. Thus, the compounds of the formula I exhibit high selectivity on application for controlling undesired plant growth in agricultural crops.

TABLE 4

Pre-emergence action of the compounds according to the invention

| Product No. | Dosage kg of a.i./ha | herbicidal action | | | |
|---|---|---|---|---|---|
| | | SIA | CRS | STM | LOM |
| 2 | 0.6 | 5 | 5 | 5 | 5 |
| 3 | 0.6 | 5 | 5 | 5 | 5 |
| 6 | 0.6 | 5 | 5 | 4 | 5 |
| 18 | 0.6 | 5 | 5 | 5 | 5 |
| 30 | 0.6 | 5 | 5 | 5 | 5 |
| 52 | 0.6 | 5 | 4 | 5 | 4 |
| 101 | 0.6 | 5 | 5 | 5 | 5 |
| 102 | 0.6 | 5 | 5 | 5 | 5 |
| 143 | 0.6 | 5 | 5 | 5 | 5 |
| 220 | 0.6 | 5 | 5 | 5 | 5 |
| 221 | 0.6 | 5 | 5 | 5 | 5 |
| 227 | 0.6 | 5 | 5 | 5 | 5 |
| 256 | 0.6 | 5 | 5 | 4 | 5 |
| 306 | 0.6 | 5 | 5 | 5 | 5 |

TABLE 5

Post-emergence action

| Product Hoe No. | Dosage kg of a.i./ha | herbicidal action | | | |
|---|---|---|---|---|---|
| | | SIA | CRS | STM | LOM |
| 2 | 0.6 | 5 | 5 | 5 | 5 |
| 3 | 0.6 | 5 | 5 | 5 | 5 |
| 6 | 0.6 | 5 | 5 | 4 | 5 |
| 18 | 0.6 | 5 | 5 | 5 | 5 |
| 30 | 0.6 | 4 | 5 | 5 | 5 |
| 52 | 0.6 | 5 | 5 | 5 | 5 |
| 101 | 0.6 | 5 | 5 | 5 | 5 |
| 102 | 0.6 | 5 | 5 | 5 | 5 |
| 143 | 0.6 | 5 | 5 | 5 | 5 |
| 220 | 0.6 | 5 | 5 | 5 | 5 |
| 221 | 0.6 | 5 | 5 | 5 | 5 |
| 222 | 0.6 | 5 | 5 | 5 | 5 |
| 256 | 0.6 | 5 | 5 | 5 | 5 |

TABLE 5-continued

| Product Hoe No. | Dosage kg of a.i./ha | Post-emergence action herbicidal action | | | |
|---|---|---|---|---|---|
| | | SIA | CRS | STM | LOM |
| 306 | 0.6 | 5 | 5 | 5 | 5 |

Abbreviations:
SIA = *Sinapis alba*
CRS = *Chrysanthemum segetum*
STM = *Stellaria media*
LOM = *Lolium multiflorum*

Inhibition of growth in cereals

In experiments on young cereal plants (wheat, barley, rye) at the 3-leaf stage, grown in dishes in the greenhouse, the plants were sprayed with compounds according to the invention at various concentrations of active substance (kg/ha) until dripping wet.

When the untreated control plants had reached a height of about 55 cm, the additional growth was measured on all plants and the growth inhibition was calculated as a percentage of the additional growth of the control plants. In addition, the phytotoxic action of the compounds was observed, with 100% denoting cessation of growth, and 0% denoting growth corresponding to that of the untreated control plants. It was evident that the compounds possess very good growth-regulating properties. The results are compiled in the table below.

TABLE 6

| Compounds of Ex. No. | Application conc. kg/ha | Inhibition of growth (%) | | | Phytotox. action |
|---|---|---|---|---|---|
| | | wheat | barley | rye | |
| 3 | 0.62 | 25 | 24 | 43 | no |
| | 0.31 | 18 | 17 | 29 | damage |
| 101 | 0.62 | 19 | 22 | 35 | no |
| | 0.31 | 15 | 17 | 29 | damage |

We claim:

1. A compound of formula I or a salt thereof $$\begin{array}{c}(R^1)_a\\\left(\begin{array}{c}CH\\||\\CH\end{array}\right)_d \quad (CH_2)_c \quad S \quad O \\ (CH_2)_e \quad N \quad SO_2 \quad NH \quad C \quad N \quad R^3 \\ (R^2)_b \qquad \qquad \qquad X \quad R^4\end{array}$$ (I)

wherein:

$R^1$ and $R^2$ independently of one another are hydrogen, halogen, or are $(C_1-C_8)$-alkyl, $(C_2-C_8)$-alkenyl, $(C_2-C_8)$-alkynyl or $(C_1-C_8)$-alkoxy each of which is unsubstituted or mono- or polysubstituted by halogen or is mono- or disubstituted by $(C_1-C_4)$-alkoxy or $(C_1-C_4)$-alkylthio; or are $-(CH_2)_n-COOR^{11}$, where n is an integer from 0 to 2, $R^3$ hydrogen, $(C_1-C_8)$-alkyl, $(C_2-C_8)$-alkenyl or $(C_2-C_8)$-alkynyl;

$R^4$ is a heterocyclic radical of formula $$\begin{array}{c}R^5\\N=\\\\-\\N\\N-\\R^6\end{array}$$

$R^5$ and $R^6$ independently of one another are hydrogen, halogen or $(C_1-C_4)$-alkyl or $(C_1-C_4)$-alkoxy, each of which is unsubstituted or mono- or polysubstituted by halogen; or are di-[$(C_1-C_4)$-alkoxy]-$(C_1-C_2)$-alkyl; $(C_3-C_6)$-cycloalkyl, $-OCHR^8COOR^9$; $-NR^9R^{10}$ or $(C_1-C_4)$-alkylthio;

$R^7$ is $(C_1-C_4)$-alkyl;

$R^8$ is hydrogen or $(C_1-C_4)$-alkyl;

$R^9$ and $R^{10}$ independently of one another are hydrogen, $(C_1-C_4)$-alkyl; $(C_2-C_4)$-alkenyl or $(C_2-C_4)$-alkynyl;

$R^{11}$ is hydrogen, or $(C_1-C_8)$-alkyl, $(C_2-C_4)$-alkenyl or $(C_2-C_4)$-alkynyl each of which is mono- or polysubstituted by halogen or $(C_1-C_4)$-alkoxy radicals;

X is oxygen or sulfur; and a, b, c, d and e independently of one another are 0, 1 or 2, with the proviso that the sum of c, d and e $\geq 2$.

2. A compound of formula I or a salt thereof as claimed in claim 1 wherein:

$R^1$ and $R^2$ independently of one another are hydrogen, halogen or $(C_1-C_4)$-alkyl which is unsubstituted, mono- or polysubstituted by halogen or mono- or disubstituted by $(C_1-C_4)$-alkoxy or $(C_1-C_4)$-alkylthio;

a and b independently of one another are 0, 1 or 2, but with the proviso that the sum of c, d and e $\geq 2$ and $\leq 4$;

$R^3$ is hydrogen, $(C_1-C_4)$-alkyl or allyl;

$R^4$ is radical of formula $$\begin{array}{c}R^5\\N=\\\\-\\N\\N-\\R^6\end{array};$$

$R^5$ and $R^6$ independently of one another are halogen, or $(C_1-C_4)$-alkyl or $(C_1-C_4)$-alkoxy each of which is unsubstituted or substituted by halogen; and X is oxygen.

3. A compound of formula I as claimed in claim 2, wherein:

$R^5$ and $R^6$ independently of one another are halogen, or $(C_1-C_4)$-alkyl or $(C_1-C_4)$-alkoxy each of which is unsubstituted or substituted by halogen; and X is oxygen.

4. A compound of formula I as claimed in claim 3, wherein:

$(R^1)_a$ is 5-methyl;

b = d = e = 0, c = 3;

$R^5$ is methoxy; and $R^6$ is methyl.

5. A compound of formula I as claimed in claim 3, wherein:

$(R^1)_a$ is 5-methyl;

b = d = e = 0, c = 3;

$R^5$ is methoxy; and $R^6$ is methoxy.

6. A compound of formula I as claimed in claim 3, wherein:
$(R^1)_a$ is 3-methyl;
$b=d=e=0$, $c=3$;
$R^5$ is methoxy; and
$R^6$ is methyl.

7. A compound of formula I as claimed in claim 3, wherein:
$(R^1)_a$ is 3-methyl;
$b=d=e=0$, $c=3$;
$R^5$ is methoxy; and
$R^6$ is 2,2,2-trifluoroethoxy.

8. A herbicidal composition comprising a herbicidally effective amount of a compound of formula I, or a salt thereof, as claimed in claim 1 and suitable carrier therefor.

9. A plant growth-regulating composition comprising a plant growth-regulating effective amount of a compound of formula I, or a salt thereof, as claimed in claim 1 and a suitable carrier therefor.

10. A method for controlling undesired plant growth which comprises applying a herbicidally effective amount of a compound of formula I, or salt thereof, as claimed in claim 1 to a plant or to an area where said plant is grown.

11. A method for regulating plant growth which comprises applying a plant growth-regulating effective amount of a compound of formula I, or a salt thereof, as claimed in claim 1 to a plant or to an area where said plant is grown.

* * * * *